United States Patent [19]

Scardera et al.

[11] 3,956,401

[45] May 11, 1976

[54] LOW FOAMING, BIODEGRADABLE, NONIONIC SURFACTANTS

[75] Inventors: Michael Scardera, Hamden; Robert N. Scott, Wallingford, both of Conn.

[73] Assignee: Olin Corporation, New Haven, Conn.

[22] Filed: Mar. 10, 1975

[21] Appl. No.: 556,746

[52] U.S. Cl. ............... 260/615 B; 252/DIG. 1; 252/DIG. 6; 252/351; 252/170; 260/459 R; 260/963
[51] Int. Cl.² ............... C07C 43/00; C07C 43/04
[58] Field of Search ............... 260/615 B

[56] References Cited
UNITED STATES PATENTS

| | | | |
|---|---|---|---|
| 3,030,426 | 4/1962 | Moseley et al. | 260/615 B |
| 3,324,035 | 6/1967 | Nankee et al. | 260/615 B |
| 3,528,920 | 9/1970 | Niizeki et al. | 260/615 B X |

Primary Examiner—Howard T. Mars
Attorney, Agent, or Firm—Kenneth P. Glynn

[57] ABSTRACT

Low foaming biodegradable, liquid, non-gelling and nonionic surfactants are claimed having the formula:

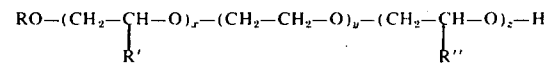

wherein R is a linear, alkyl hydrocarbon having an average from about 7 to 10 carbon atoms, R' is a linear, alkyl hydrocarbon of about 1 to about 4 carbon atoms, R'' is a linear, alkyl hydrocarbon of about 1 to about 4 carbon atoms, $x$ is an integer of about 1 to about 6, $y$ is an integer of about 4 to about 15 and $z$ is an integer of about 4 to 25.

11 Claims, No Drawings

LOW FOAMING, BIODEGRADABLE, NONIONIC SURFACTANTS

This invention relates to novel low foaming, biodegradable, nonionic surfactants which are liquid at room temperature and non-gelling in water solution.

The surface active agent art is quite old and replete with different compositions of useful ionic and nonionic surfactants. An early patent to Schuette et al., U.S. Pat. No. 2,174,761, broadly discloses the preparation of high molecular weight surfactants by the sequential addition of propylene oxide and ethylene oxide to long chain hydrophobic alcohols and specifically discloses the production of surfactants which are solids at room temperature. More recent patents to Lunsted, U.S. Pat. No. 2,674,619 and Jackson et al., U.S. Pat. No. 2,677,700 show surfactant compositions prepared by the addition of propylene oxide and ethylene oxide to a reactive hydrogen compound. Schick discloses the more recent history of nonionic surfactants in his book "Nonionic Surfactants", 1967. Canadian Patent No. 540,359 describes conjugated polyoxypropylene-polyoxyethylene compounds as surfactants which are prepared by condensing propylene oxide with an alcohol to obtain a polyoxypropylene intermediate polymer and subsequently condensing ethylene oxide with the intermediate polymer to obtain the final product. The Canadian patent requires the use of an alcohol which has a detergency factor of less than 100, i.e., alcohols, if linear, having six or less carbon atoms.

Recent environmental problems have placed particular emphasis on surfactants that are biodegradable. Biodegradability is defined as that property possessed by a material which is capable of being decomposed by bacteria or living organisms, as described for example in the patent to Egan et al., U.S. Pat. No. 3,382,285. While the prior art, as noted above, has disclosed a large number of surfactant products having a wide variety of properties, there has been some difficulty in obtaining a surfactant which has the normal properties required by such products, and is also biodegradable. There is also a desire to obtain biodegradable surfactants which are liquid at room temperature, are low foaming and are non-gelling in water solution. Such properties would make the surfactant products easier to handle and store and also would permit greater preparation and processing versatility. However, most nonionic surfactants and particularly biodegradable ones generally have a tendency to form gels when placed in water particularly when in concentrated amounts.

Now it has been found that the compounds of this invention have the normal characteristics and properties required of surface active agents and additionally and significantly are low foaming, biodegradable, liquid at room temperature and non-gelling in water solutions. More particularly, the surfactant compositions of this invention have the formula:

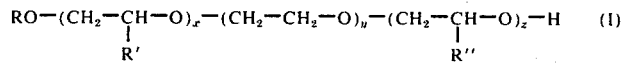

wherein R is a substantially linear hydrocarbon and more particularly an alkyl group having an average of from about 7 to about 10 carbon atoms, preferably from about 8 to about 9 carbon atoms, R' is a linear, alkyl hydrocarbon of from about 1 to about 4 carbon atoms, and preferably has 1 to 2 carbon atoms, and is most desirably a methyl group, R" is a linear, alkyl hydrocarbon of from about 1 to about 4 carbon atoms, preferably 1 to 2 carbon atoms and most desirably 1 carbon atoms, X is an integer of about 1 to about 6 and preferably about 2 to about 4, y is an integer of about 4 to about 15 and preferably about 5 to about 12, and z is an integer of about 4 to about 25 and preferably about 6 to 20.

The R group, as noted above, is substantially or predominantly linear which means there is essentially no branching. This is important because the biodegradability of the product is detrimentally affected by branching. However, as will be described in more detail below, the R group is derived from a linear alcohol and generally from a mixture of alcohols. Due to the nature of the process by which these alcohols are prepared, there may be small amounts of branched chain alcohols present. Generally, the presence of such branched chain alcohols in amounts less than about 15% of the total alcohol content by weight, will not adversely effect the overall properties of the final product. The terms linear or substantially linear hydrocarbon when used in the specification and claims with respect to R are intended to include such small amounts of branching as defined above. The number of carbon atoms referred to for R is an average number since commercial grade alcohols are generally a mixture of more than one alcohol. Preferably the R group will have an average of about 8 to 9 carbon atoms.

The values of the $x$, $y$, and $z$ integers are actually average numbers determined by the weight of that particular reactant which is used.

The surfactant compounds (I) may be prepared by the well-known methods of adding an alkylene oxide compound to an alcohol as shown for example in Schick's "Nonionic Surfactants" at page 102 and in U.S. Pat. No. 2,677,700 at Column 6. Generally, the compounds (I) may be prepared by reacting a primary, linear, monohydric alcohol having from about 7 to 10 carbon atoms with an alkylene oxide such as propylene oxide in the desired amounts at an elevated temperature in the presence of alkaline catalysts such as the salts or hydroxides of the alkali metals or the alkaline earth metals. Following this, ethylene oxide is added in the desired amounts using the same conditions to obtain an intermediate alcohol-polyoxyalkylenepolyoxyethylene reaction product. Next, an alkylene oxide, such as propylene oxide, is reacted with the intermediate product in the desired amounts, by again using the same type of catalyst and reaction conditions, to obtain the low foaming surfactant products of the present invention.

As noted above, the alcohol used is a primary linear alcohol having 7 to 10 carbon atoms. A mixture of such alcohols may be used and this is generally true when using commercial alcohols which are often available as a blend of several alcohols. Consequently, the number of carbon atoms in the alcohol is referred to as an average number and such number can be determined by vapor phase chromatography (VPC) and the hydroxyl number. Also, as noted above, while the alcohols are referred to as linear, there may be some minor amount of branching particularly due to the method of manufacture. Following are some of the useful alcohols: heptyl alcohol, octyl alcohol, nonyl alcohol, decyl alcohol, mixtures of these which may include, for example, hexyl alcohol, and well-known commercial mixtures such as Alfol 610 having an average of about 8.2 carbon atoms (about 22% of $C_6$, 39% of $C_8$ and 38% of $C_{10}$) produced by Continental Oil, and P & G's I 12 (about 20% of $C_6$, 36% of $C_8$ and 35% of $C_{10}$) produced by Proctor and Gamble. Further illustrations of such alcohols and of the method of preparation are shown in Schick's "Nonionic Surfactants" at pages 87–90.

The alcohols used as one of the reactants in preparing the surfactants of the present invention, in addition to being generally primary, linear, monohydric alcohols having an average number of carbon atoms of about 7 to 10 and preferably about 8 to 9, have a detergency factor of greater than 100. By using an alcohol or a mixture of alcohols having a detergency factor of greater than 100, yet having an average number of carbon atoms no greater than 10, nonionic surfactants are obtained which are liquid at room temperature, are non-gelling in water solutions and are biodegradable. Additionally, by adding a hydrophobic component to the end of the polyoxyethylene hydrophile in the surfactants of the present invention, advantageous low foaming properties are also obtained.

In preparing the surfactants of the present invention, a temperature of about 140° to about 200°C. may be used in the reaction and the catalyst concentration can be varied widely with about 0.001 to about 1% by weight of catalyst based on the weight of alcohol being generally used. While the reaction may be carried out at atmospheric pressure, it may also be performed under elevated pressure conditions if desired.

The surfactant products (I) of this invention may be used in a variety of application such as detergent formulations, as wetting, washing, dispersing, etc., agents in the textile, leather, paper, paint, pharaceutical and cosmetic industries, etc., as well as for household applications. These products can also be used as intermediates for preparing anionic surfactants such as sulfates and phosphates.

The following examples are presented to further illustrate the invention without any intention of being limited thereby.

EXAMPLE 1

Into a 3-necked, 500 ml. round bottom flask fitted with a dropping funnel, nitrogen inlet, stirrer, dry ice condenser and vent, 134 grams (1 mole) of Alfol 610 alcohol (detergency factor: 140 ± 5) and 0.7 grams (0.012 mole, 0.5% based on the weight of alcohol) of potassium hydroxide were added. Under a nitrogen atmosphere, 174 grams (3 moles) of propylene oxide was added dropwise to the alcohol at 160° to 180°C. Upon completion of the propylene oxide addition, the reaction mixture was cooled, and it was determined that the product had an alcohol to propylene oxide (PO) ratio of 1:3.

A portion of the alcohol - PO adduct, 30.8 grams (0.1 mole), was then charged to a 3-necked, 500 ml. round bottom flask fitted with similar equipment as described above. 55.1 Grams (1.25 moles) of ethylene oxide was then added dropwise at 160° to 180°C. under a nitrogen atmosphere until completion. The resulting intermediate product was found to have an alcohol to propylene oxide to ethylene oxide of about 1:3:12.5.

Next, 43.2 grams (0.05 mole) of the Alfol 610 propylene oxideethylene oxide adduct intermediate product, with catalyst, was charged to a 3-necked, 500 ml. round bottom flask with equipment and conditions as above. 42.6 Grams of propylene oxide was added dropwise under a nitrogen blanket at a temperature of about 160° to 170°C. The product was subsequently cooled and neutralized with acetic acid. The product weight was 62.7 grams and the cloud point of a 1% water solution of the product was 64°C. The molecular weight of the final product was found to be 1710, with an alcohol to propylene oxide (PO) to ethylene oxide (EO) to propylene oxide (PO) ratio of 1:3:12.5:14.7.

Concentrations of from 0 to 100% by weight surfactant in water solution at room temperature did not form a stable gel.

Example 1 may be repeated substituting a higher alkylene oxide for the propylene oxide in preparing the adduct of the first step and/or substituting a higher alkylene oxide for the propylene oxide in the last step of preparing the surfactants of the present invention. For example, 3 moles of butylene oxide or hexylene oxide may be substituted for the 3 moles of propylene oxide used in the first step of Example 1 above. Also, about 0.75 moles of butylene oxide or hexylene oxide may be substituted for the propylene oxide used in the last step of Example 1 above.

EXAMPLES 2–9

The procedure of Example 1 was repeated for Examples 2–9, except that various amounts of ethylene oxide and last step propylene oxide were used. The following Table illustrates the cloud point and surface tension characteristics of the products obtained:

TABLE

| | Low Foaming Surfactant Properties | | |
|---|---|---|---|
| Example | Alfol-PO-EO-PO Mole Ratios (rounded off to integers) | Cloud Point (1% Solution) °C. | Surface Tension (dynes/cm) 0.1% |
| 1 | 1-3-12-15 | 23 | 31.9 |
| 2 | 1-3-7-7 | 24 | 30.8 |
| 3 | 1-3-7-10 | 18 | 31.6 |
| 4 | 1-3-7-6 | 24 | 30.5 |
| 5 | 1-3-12-15 | 24 | 32.3 |
| 6 | 1-3-12-22 | 14 | 32.2 |
| 7 | 1-3-12-10 | 35 | 31.5 |
| 8 | 1-3-12-18 | 19 | 32.5 |
| 9 | 1-3-12-14 | 30 | 30.7 |

Detergency Factor Determinations

To illustrate that the alcohols employed in the present invention have detergency factors greater than 100, the following detergency factor determinations were made:

Ethylene oxide was added to hexanol ($C_6$), heptanol ($C_7$), hexanol + 3 moles propylene oxide, and Alfol 610 (a mixture of $C_6$, $C_8$, $C_{10}$ alcohols, ave. $C_{8.2}$) to prepare oxyethylene adducts containing 20 ± 2%, 30 ± 2%, 40 ± 2%, 50 ± 2% and 60 ± 2% oxyethylene content. Distilled water solutions with an adduct content of 0.25% by weight were prepared for each and placed in a Tergotometer at 140°F. Control surfactants were the hexanol + 3 PO ethoxylate and an alkyl benzene sulfate. Both of these controls are stated to have an arbitrary detergency factor of 100 according to Canadian Patent No. 540,359. A Tergotometer was operated at 100 rpm using Testfabrics, Inc. cotton swatches soiled with oil and carbon black. The swatches (2) were washed for 10 minutes, rinsed and ironed. Reflectance measurements were then read with a Photovolt Reflectance Meter with a green filter. The readings were then multiplied by a factor to obtain the arbitrary detergency factor of 100 for hexanol + 3 PO ethoxylate as stated in Canadian Patent No. 540,359. The following results were obtained:

|  | DETERGENCY FACTOR |
| --- | --- |
| Hexanol Ethoxylate | 70 ± 5 |
| Alkyl Benzene Sulfonate | 85 ± 5 |
| Hexanol + 3 PO Ethoxylate | 100 ± 5 |
| Heptanol Ethoxylate | 120 ± 5 |
| Alfol 610 Ethoxylate ($C_{8.2}$) | 140 ± 5 |

What is claimed is:

1. A surfactant product having the forumula:

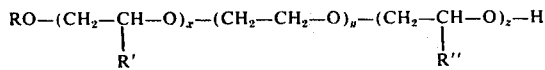

wherein R is a linear, alkyl hydrocarbon having an average of from about 7 to about 10 carbon atoms, R' is a linear, alkyl hydrocarbon of about 1 to about 4 carbon atoms, R'' is a linear, alkyl hydrocarbon of about 1 to about 4 carbon atoms, $x$ is an integer of about 1 to about 6, $y$ is an integer of about 4 to about 15, and $z$ is an integer of about 4 to about 25.

2. The surfactant product of claim 1 wherein R has an average of about 8 to 9 carbon atoms.

3. The surfactant product of claim 1 wherein R' has about 1 to 2 carbon atoms.

4. The surfactant product of claim 1 wherein R'' has about 1 to 2 carbon atoms.

5. The surfactant product of claim 1 wherein both R' and R'' have about 1 to 2 carbon atoms.

6. The surfactant product of claim 5 wherein both R' and R'' are methyl groups.

7. The surfactant product of claim 1 wherein $x$ is about 2 to 4, $y$ is about 5 to 12 and $z$ is about 6 to 20.

8. The surfactant product of claim 7 wherein both R' and R'' have about 1 to 2 carbon atoms.

9. The surfactant product of claim 8 wherein R' and R'' are methyl groups.

10. The surfactant product of claim 9 wherein R has an average of about 8 to 9 carbon atoms.

11. The surfactant product of claim 10 wherein $x$ is 3.

* * * * *